(12) United States Patent
Dunki-Jacobs et al.

(10) Patent No.: US 7,442,167 B2
(45) Date of Patent: Oct. 28, 2008

(54) INTEGRATED VISUALIZATION SYSTEM

(75) Inventors: Robert Dunki-Jacobs, Mason, OH (US); Scott D. Wampler, West Chester, OH (US); Trevor W. V. Speeg, Williamsburg, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/331,775

(22) Filed: Jan. 13, 2006

(65) Prior Publication Data

US 2006/0116553 A1 Jun. 1, 2006

Related U.S. Application Data

(63) Continuation of application No. 10/393,580, filed on Mar. 21, 2003, now abandoned.

(60) Provisional application No. 60/366,727, filed on Mar. 22, 2002.

(51) Int. Cl.
*A61B 1/07* (2006.01)
*A61B 1/05* (2006.01)

(52) U.S. Cl. ............... 600/179; 600/129; 600/177; 600/182

(58) Field of Classification Search ............... 600/109, 600/130, 129, 160, 176–179, 182; 362/555, 362/574
See application file for complete search history.

(56) References Cited

U.S. PATENT DOCUMENTS

| | | | | |
|---|---|---|---|---|
| 4,053,756 A * | 10/1977 | Takahashi | ............... | 362/7 |
| 4,414,962 A | 11/1983 | Carson | | |
| 4,678,900 A * | 7/1987 | Nishioka | ............... | 250/205 |
| 5,335,662 A | 8/1994 | Kimura et al. | | |
| 5,929,901 A | 7/1999 | Adair et al. | | |
| 6,063,024 A | 5/2000 | Yamamoto | | |
| 6,124,883 A | 9/2000 | Suzuki et al. | | |
| 6,139,489 A * | 10/2000 | Wampler et al. | ............... | 600/109 |
| 6,260,994 B1 | 7/2001 | Matsumoto et al. | | |
| 6,478,730 B1 * | 11/2002 | Bala et al. | ............... | 600/121 |
| 6,626,825 B2 * | 9/2003 | Tsai | ............... | 600/109 |
| 6,730,019 B2 | 5/2004 | Irion | | |
| 6,805,665 B1 | 10/2004 | Tatsuno et al. | | |
| 6,902,527 B1 | 6/2005 | Doguchi et al. | | |
| 2002/0030444 A1 | 3/2002 | Muller-Mach et al. | | |

(Continued)

FOREIGN PATENT DOCUMENTS

WO    WO 94/13191 A    6/1994

(Continued)

OTHER PUBLICATIONS

European Search Report dated May 31, 2007 for corresponding patent application, European Patent Application No. EP03718036.

*Primary Examiner*—John P. Leubecker
(74) *Attorney, Agent, or Firm*—Verne E. Kreger, Jr.

(57) ABSTRACT

An endoscope that has an integrated light source and camera mounted at the distal end of the endoscope. The light source is a class of LED devices constructed of high-efficiency LEDs that emit narrow-band blue light coupled with phosphors, which cause a nearly natural "white" light to be emitted. The LEDs are coupled to a waveguide for transmission of the light to the distal end of the endoscope.

13 Claims, 11 Drawing Sheets

U.S. PATENT DOCUMENTS

| | | |
|---|---|---|
| 2002/0103417 A1 | 8/2002 | Gazdzinski |
| 2002/0115918 A1* | 8/2002 | Crowley ..................... 600/310 |
| 2002/0135694 A1 | 9/2002 | Williams |
| 2002/0143239 A1* | 10/2002 | Henzler ..................... 600/179 |
| 2002/0193664 A1 | 12/2002 | Ross et al. |
| 2003/0028078 A1* | 2/2003 | Glukhovsky ................ 600/109 |
| 2003/0050534 A1 | 3/2003 | Kazakevich |

FOREIGN PATENT DOCUMENTS

| | | |
|---|---|---|
| WO | WO 95/15060 | 1/1995 |

* cited by examiner

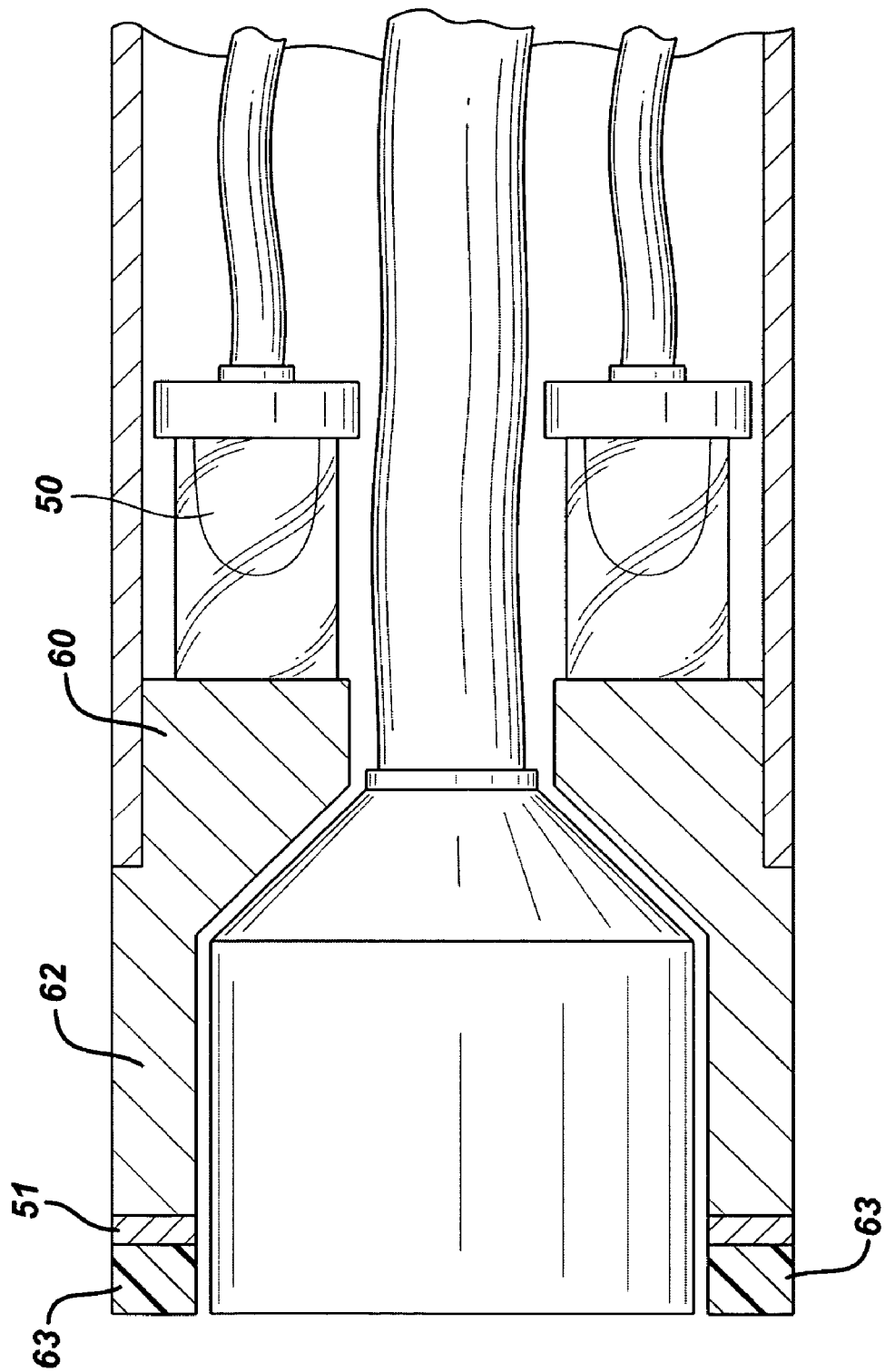

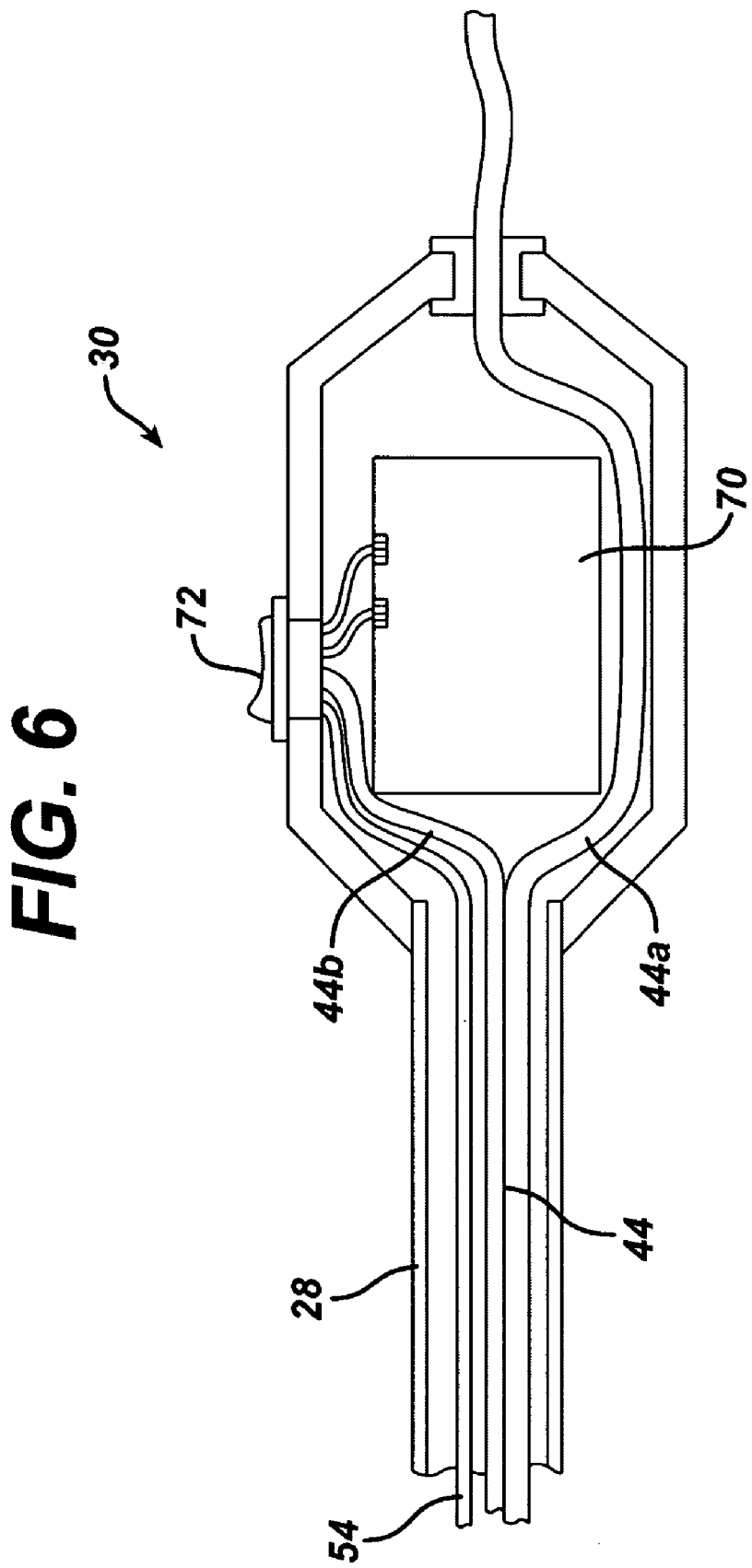

INTEGRATED VISUALIZATION SYSTEM

RELATED PATENT APPLICATIONS

The present application is a continuation of U.S. patent application, Ser. No. 10/393,580, filed on Mar. 21, 2003, now abandoned, which claims priority to U.S. Provisional Application Ser. No. 60/366,727 filed Mar. 22, 2002, the entire disclosure of which is incorporated herein by reference.

FIELD OF THE INVENTION

The present invention relates in general to a video scope, and more particularly, to a endoscope useful for medical procedures that has a self-contained camera and light source.

BACKGROUND OF THE INVENTION

Endoscopes are used with increasing frequency in operating rooms. They have facilitated the growth of new minimally invasive procedures that allow surgery to be done through small openings into internal body cavities created by trocars and into external body cavities through the mouth and anus. The vision necessary to do minimally invasive surgery is accomplished by inserting endoscopes equipped with video cameras (video endoscopes) that display full motion images on a video monitor. These monitors are placed near the operative field where the surgeon can see them.

Although video endoscopes and the associated equipment help facilitate these minimally invasive procedures there are several factors about these systems that are currently undesirable. The most important are; i) the bulk of the equipment that is necessary to create and display the images and their proximity to the operative site and ii) the location and number of interconnecting elements. Traditional endoscopes require the use of a collection of electronic components commonly referred to as a video tower. This rack of equipment includes several electronic components that provide functions such as: processing of video signals from the camera, supplying power to the tower-based equipment and the camera, supplying visible light energy to the endoscope and displaying the video images to the surgeon. The video endoscope itself is connected to this video tower through a camera wire and an optical fiber bundle that serves as a light transmission source. This optical fiber bundle is necessary to carry light from the tower-based source to the endoscope. Due to the light losses inherent to the optical fiber bundle, they are typically no longer than six feet. The lengths of these interconnecting cables require that the video tower be forced to be in the footprint of the operative site. Using current technology, the video tower takes up significant space near the patient and the operating room staff. In addition, the optical fiber bundles heavy enough to which make the endoscope hard to manage.

As minimally invasive instruments become more advanced there is a drive to create instruments that go through smaller ports, and thus leave smaller wounds in the patient. Video Endoscopes must keep pace with this decrease in cross section.

Because of these drawbacks in the traditional video endoscope systems, there have been new designs that have tried to remove as many of the external equipment in the system as are possible. This would take equipment out of the footprint of the operative area. One example includes scope designs that remove the external light source from the video endoscope systems. In, for example, U.S. Pat. No. 5,908,294 by Schick et al. and U.S. Pat. No. 6,190,309 by Ooshima et al white light sources, specifically white light emitting diodes (LEDs), are placed at the distal end of the video endoscope to provide illumination to the operative site. This arrangement eliminates the need to have an external light source or a fiber optic cable. Because the light sources in this embodiment are placed distal to the camera itself and must still be within the cross section of the instrument, Video endoscopes so configured do not have the ability to view axially, as would be needed in endoscopic procedures. In this embodiment, only video endoscopes that view in directions away from the axis of the shaft of the instrument are possible. See, for example, U.S. Pat. No. 5,908,294 by Schick et al. and U.S. Pat. No. 6,190,309 by Ooshima et al.

An improved video endoscope system would be one that removes the need for external equipment such as light sources and the associated connection cables, while still allowing the video endoscope to view axially relative to the shaft of the instrument. A further advantage of an improved video endoscope system would be one that had an entirely wireless design enabled by operation from battery power supplies and video data communications via modulated electromagnetic energy or modulated visible or invisible light. Such a system would have no need for support equipment within the footprint of the operative area except for the compatible video data receiver and a display monitor.

SUMMARY OF THE INVENTION

The present invention advantageously avoids the aforementioned drawbacks of the prior art by providing a novel light source arrangement in combination with a light guide and camera located, in one embodiment, at the distal end of the endoscope that results in a conveniently packaged video scope for use in medical surgical procedures.

In one aspect of the invention, the light source is a class of LED devices constructed of high-efficiency LEDs that emit narrow-band blue light coupled with phosphors, which cause a nearly natural "white" light to be emitted. The LEDs are coupled to a waveguide for transmission of the light to the distal end of the endoscope.

In an alternate embodiment of the invention, a camera/light unit attaches to the proximal end of the endoscope and provides for an LED light source to be communicated to the endoscope.

The present invention has, without limitation, application in conventional endoscopic and open surgical instrumentation as well as application in robotic-assisted surgery.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 5C is an alternate embodiment of the light guide and light source integrated within the end-effector and tubular portion of the present invention;

FIG. 6 shows a cut-away view of the body and the proximal end of the tubular portion of the present invention endoscope;

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. Further, it is understood that any one or more of the following-described embodiments, expressions of embodiments, examples, methods, etc. can be combined with any one or more of the other following-described embodiments, expressions of embodiments, examples, methods, etc.

Figure 1:
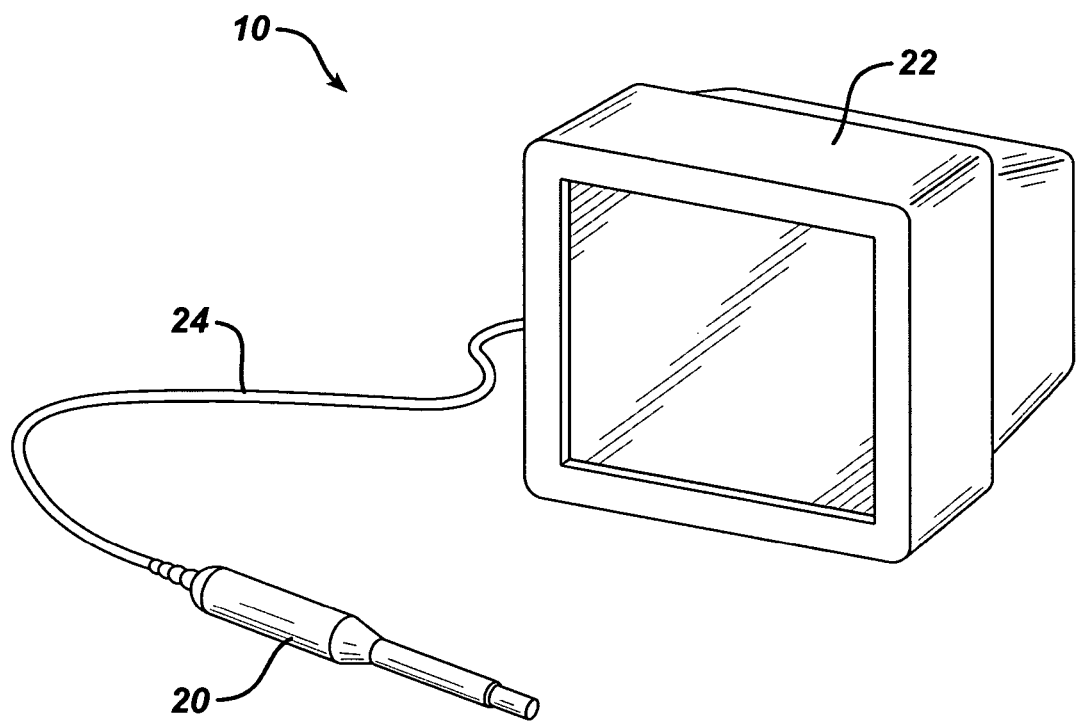
FIG. 1 is an isometric view of an video endoscopic system configured as a rigid laparoscope.

FIG. 1 shows an isometric view of a video endoscopic system 10 configured as a rigid laparoscope. This system 10 includes an endoscope 20, a monitor 22 and a connector cable 24 between the two. The endoscope 20 has both lighting and imaging capabilities incorporated into it. The system will illuminate the operative field and generate a video image stream that can be transferred from the video endoscope 20 by the connector cable 24 and viewed on the monitor 22 by the user.

Figure 2:
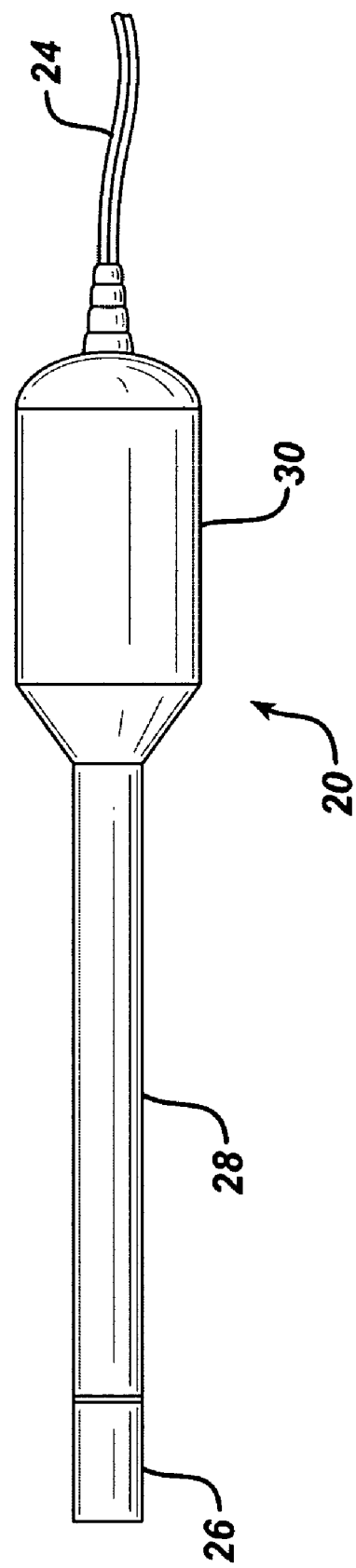
FIG. 2 shows a side view of the present invention endoscope.

FIG. 2 shows a side view of the endoscope 20. The endoscope 20 comprises an end-effector 26, a tubular portion 28 and a body 30. The connector cable 24 is connected to the body 30 of the endoscope 20. For a rigid laparoscope, the end-effector 26 and tubular portion 28 is designed so that it will fit through a standard entry port, such as a trocar, for laparoscopic surgery.

Figure 3:
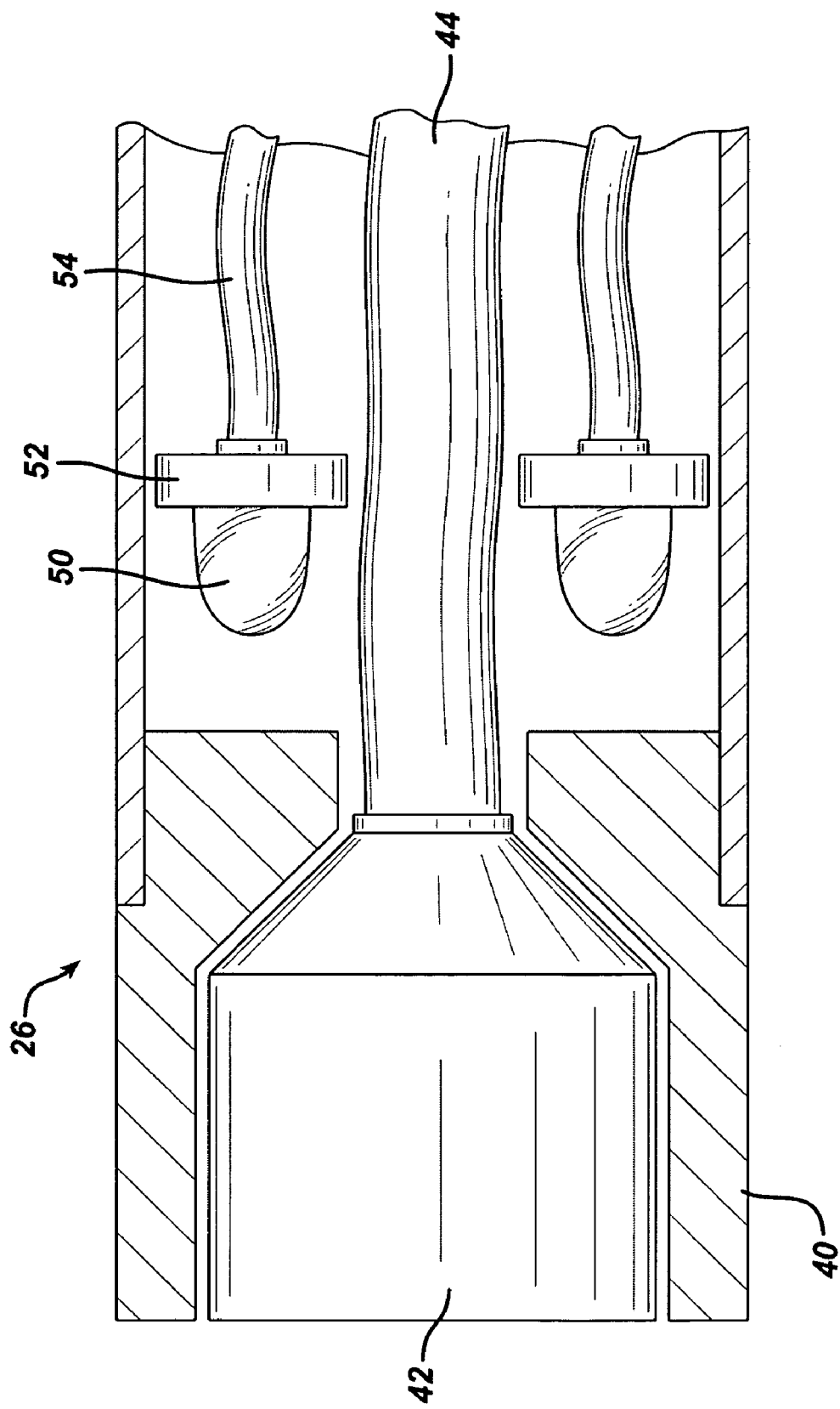
FIG. 3 shows a cut-away view of the end-effector and the distal end of the tubular portion of the present invention.

Referring now to FIG. 3 the end-effector 26 comprises a light guide 40, a camera 42 and a camera connector 44. The camera 42 is positioned concentric to the light guide 40 and is connected to the body 30 by the camera connector 44. Non-symmetric configurations are also possible. The camera connector 44 supplies power to the camera 42 and transfers the image generated by the camera 42 proximally to the body 30. A light source 50 is integrated within the tubular portion 28, but could be integrated anywhere within the video endoscope 20. The light source 50 is a white light source that is compatible to the camera 42 for optimal picture quality. In the preferred embodiment the white light source is white light LEDs that are constructed from blue light LED elements packaged with a phosphorus coating. When these blue LEDs emit their blue light onto the phosphorus coating, the coating emits light in the full white light spectrum. An alternative light source is tungsten style gas filled bulbs.

The light source 50 is mounted on a light source mounting board 52 that is optimally positioned within the tubular portion and puts it at an optimal position to couple light into the light guide 40. The light guide 40 is designed to concentrate the light generated by the light source 50 and allow it to pass around the camera and out of the distal end of the video endoscope 20. The light source power cable 54 supplies power from the power source (not shown) to the light source 50 and is connected to it by the light source mounting board 52.

Figure 4:
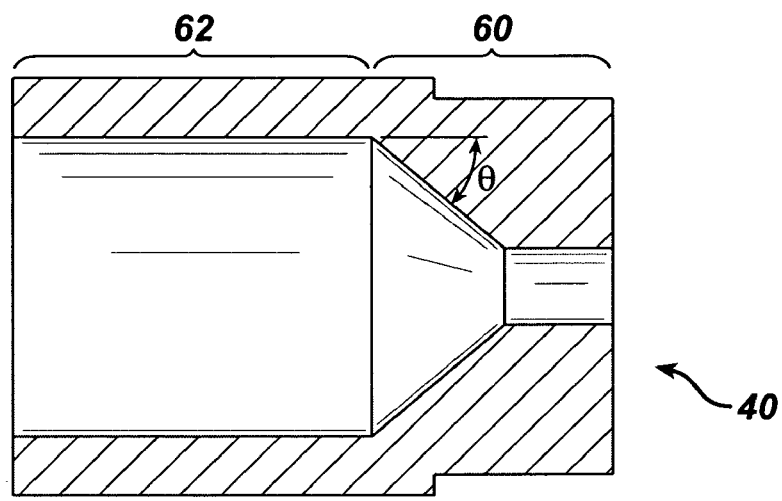
FIG. 4 shows a cross section view of one embodiment of the light guide.

FIG. 4 shows a cross section of the light guide 40. In a preferred embodiment the light guide 40 is constructed in one piece of a molded plastic such as polycarbonate. In alternative embodiments however, the light guide could be constructed of a variety of translucent materials such as glass or it could be made in a plurality of radial segments that ran along the axis of the device such as optical fibers. The light guide 40 comprises a concentrating portion 60 and a transmission portion 62. The concentrating portion 60 is further comprised of a reflecting angle ?. The reflecting angle ? is designed to be under the critical angle of the material that the light guide 40. Snell's Law dictates that any light that strikes an interface between two materials shall be totally internally reflected if it strikes the interface at an angle greater than the critical angle. This critical angle is calculated based on the difference in indexes of refraction between the two materials. For a typical plastic/air interface the critical angle is approximately 46-49 degrees. For the preferred embodiment with a single molded polycarbonate light guide a preferred angle would be approximately 50-60 degrees for optimal performance. It is known in the art that applying a cladding to the surface of the light guide could greatly improve the efficiency of the transmission of light by creating a plastic/cladding interface that has a significantly smaller critical angle than with the plastic/air interface. Optical fibers use this theory by adding doping chemicals to the plastic to create the cladding layer. This total internal reflection will cause the light to be gradually concentrated and passed onto the transmission portion 62 with minimal losses. The transmission portion 62 is designed so as to be of limited cross sectional area to minimize its profile without generating losses in the light that is transmitted through it. An alternative light guide could be as described above (with or without cladding) with the addition of chemical elements in a controlled manner to the external surfaces that create a gradient in the index of refraction to reduce optical loss through the plastic/air interface at all points.

Figure 5A:
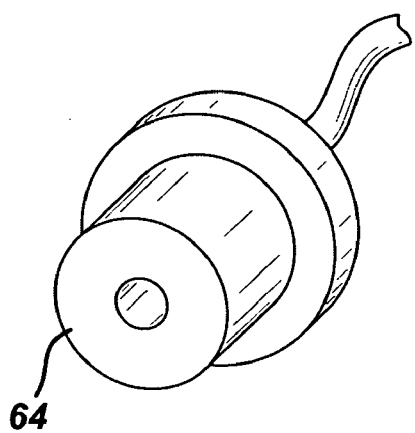
FIGS. 5A-B show two alternate embodiments of the lighting system that is integrated inside the tubular portion of the video endoscope.
Figure 5B:
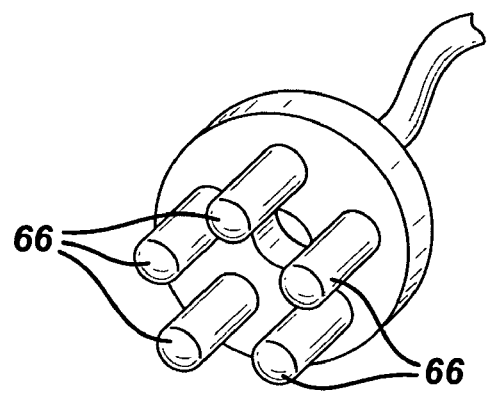

FIGS. 5A-B show two alternate embodiments of the lighting system that is integrated inside the tubular portion 28. In FIG. 5A the light source 64 is a single package that contains multiple light source elements. In FIG. 5B the light source 66 is a plurality of packages that each contain a single light source element. The light source in FIG. 5B could be standard LED packages, such as a T1 LED package, that are grouped together at maximum density. FIG. 5A shows an improved LED packaging scheme whereby multiple blue LED elements and connected in a circuit and packaged within one housing that has phosphorus coating on it. This embodiment allows for a higher density of LED elements in the same space than can be achieved through utilization of the off the shelf designs. This would greatly enhance the illumination power of the light source 50 and allows the video endoscope 20 to view images at a greater distance or with increased image quality. In FIG. 5C, the phosphorus coating 51 is removed from the light source 50 and is placed at the distal portion of the transmission portion 62 with an additional plastic interface 63 at the most distal point to isolate the phosphorous coating from the external environment.

FIG. 6 shows a cross section view of the body 30 and the proximal end of the tubular portion 28. The proximal end of the tubular portion 28 is connected to the distal portion of the body 30. The body further comprises a power source 70 and a control switch 72 located on the outside of the body and is accessible by the user. The power source 70 can be any version of a wireless power supply that is known in the art, such as a battery. The camera connector 44 and light source connector cable 54 passes from the camera 42 and light source 50, respectively, at the distal end, through the tubular portion 28 and into the body 30. As the camera connector 44 passes into the body 30 it divides into two different leads, the camera source power cable 44b and the video signal and control cable 44a. The camera and light source power cable 44b and 54 attach to the control switch 72 and the signal cable 44a passes through the body and exits on the proximal end. As it exits the proximal end of the body it becomes the connector cable. The user manipulates the control switch 72 so that the power delivered to the light source is varied, thereby controlling illumination level. When the light source 50 is off, power is removed from the camera 42 in the end effector. The signal cable 44a carries the image signal from the camera 42 to the monitor 22 via connector cable 24.

Figure 7:
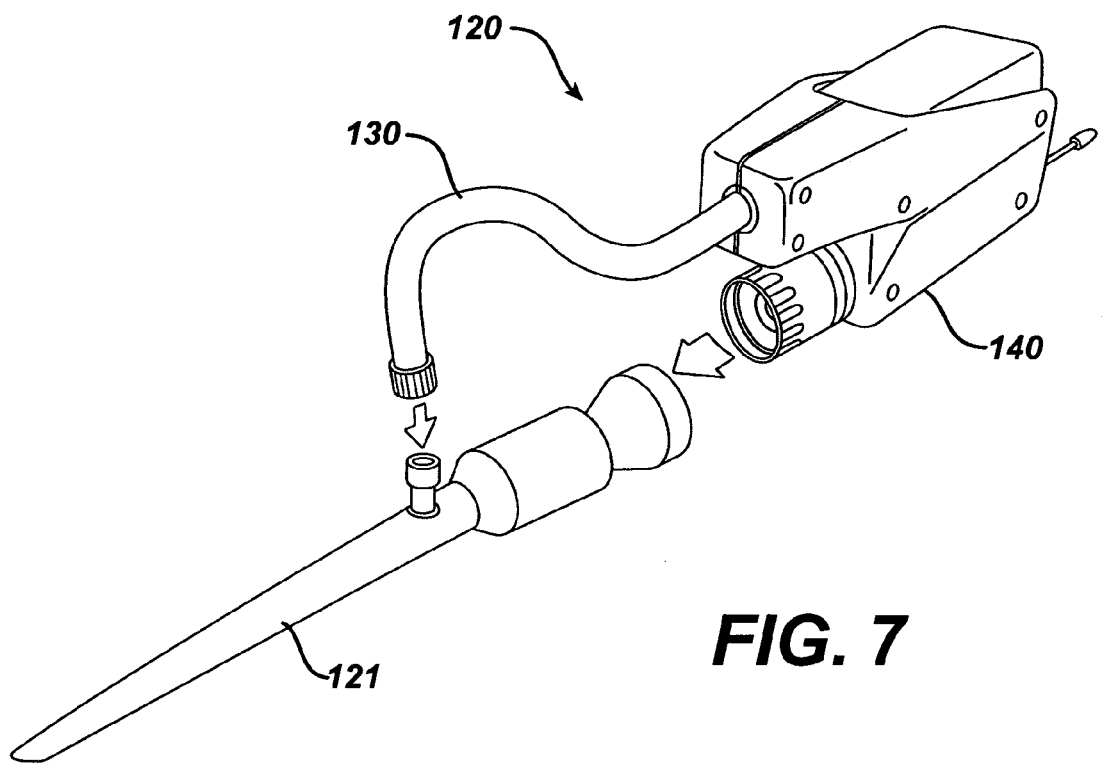
FIG. 7 shows a second embodiment of the present invention video endoscope.

FIG. 7 shows a second embodiment of a video endoscope system 120. The endoscope system 120 comprises an endoscope 121 light cable 130 and a camera/light unit 140. The camera/light unit 140 attaches to the proximal end of the endoscope 121. The light cable 130 attaches to the camera/light unit 140 at its proximal end, while its distal end attaches to the light source port of the endoscope 121. The camera/light unit 140 contains the imaging system, light system and signal transmission means for the endoscope 121. In the preferred embodiment, the signal transmission means could be a RF transmitter such as the 1.4 GHz transmitters used with wireless security cameras. The transmission means could alternatively be one of several methods of transmission protocols that are known to those skilled in the art, such as the Bluetooth system.

Figure 8:
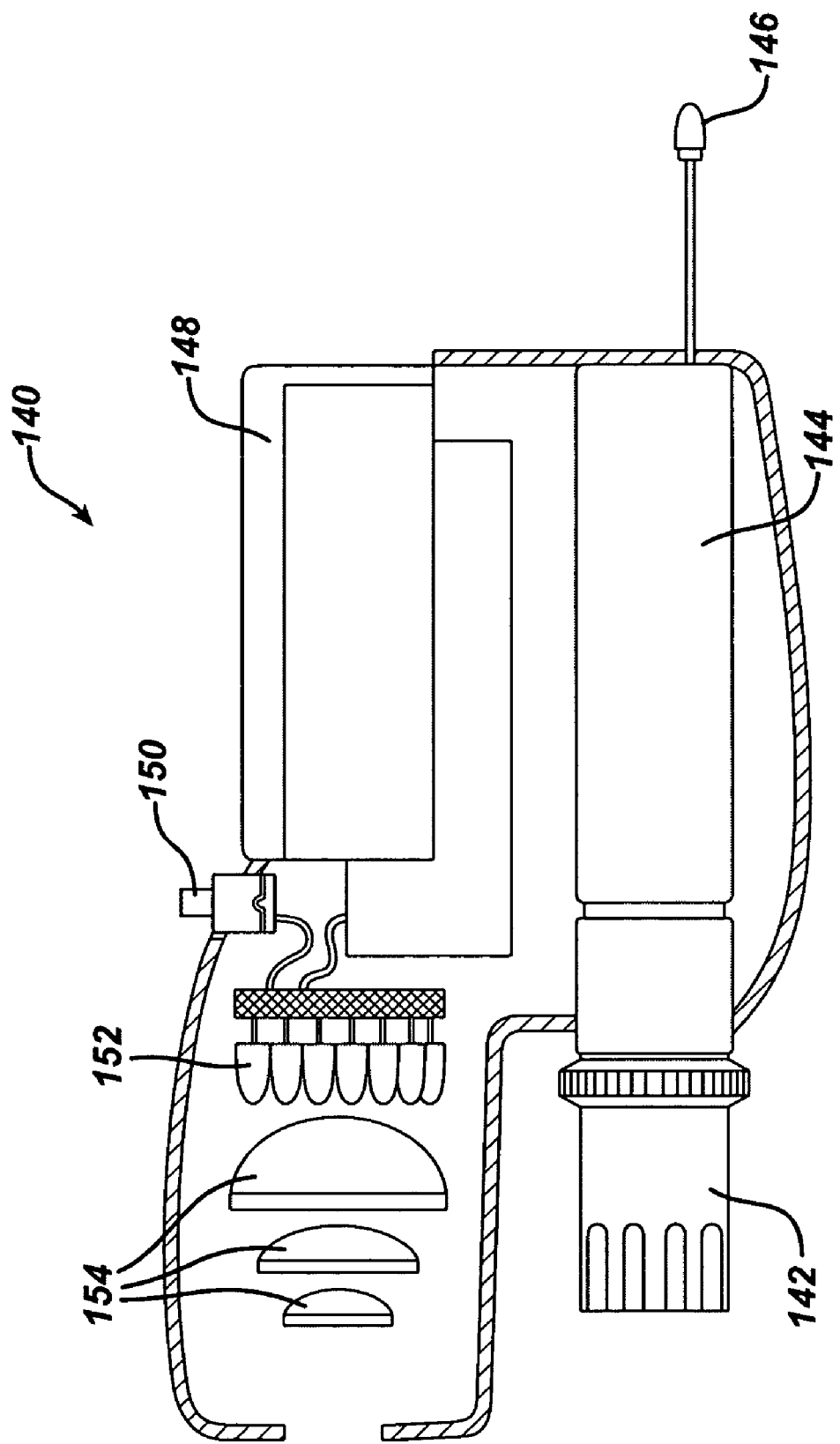
FIG. 8 shows a cross sectional view of the camera/light unit of the embodiment shown in FIG. 7.

Referring now to FIG. 8, the camera/light unit 140 comprises an endoscope adapter 142, camera, 144 signal transmission means 146, power source 148, control switch 150, white light source 152 and focusing lens 154. These are all contained within the body of the camera/light unit 140. The endoscope adapter 142 is designed in such a way as to be operatively connected to the endoscope 121 to couple its optics into the camera. The camera 144 receives the image from the optics of the endoscope 121 and convert it into a video signal. The signal transmission means 146 is operatively connected to the camera 144 in order to take its video signal and transmit it to a remote receiver. Though this is shown in FIG. 8 as a wireless connection, it is obvious that it could be a hard-wired connection. The power source 148 supplies power to the white light source 152 and the camera unit 144 through its connection that passes through the control switch 150. The focusing lens 154 gathers the light generated by the white light source 152 and concentrates it to a smaller cross sectional area so that it can be efficiently coupled into the light cable 130 that connects to the camera/light unit at this port. An alternative embodiment would be constructed form a plurality of blue LED die covered by a phosphorus coating and a plurality of focusing lens elements approximated to the light cable attachment.

Figure 9:
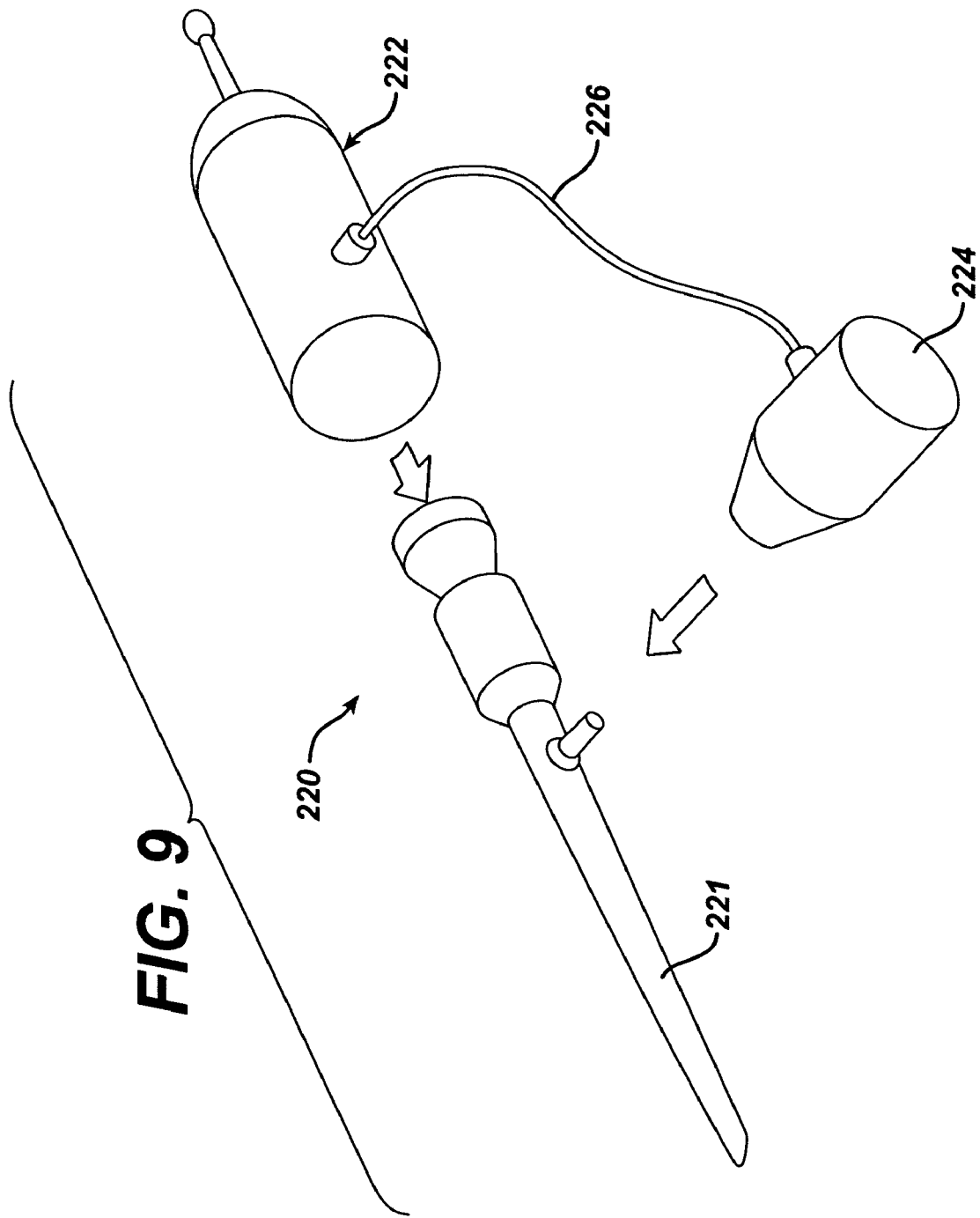
FIG. 9 shows an isometric view of an alternate embodiment of the present invention video endoscope.

FIG. 9 shows an isometric view of a third embodiment of a video endoscope system 220, which comprises an endoscope 221, a camera unit 222, a light unit 224 and a power cord 226. The power cord 226 connects the camera unit 222 to the light unit 224 and passes power to the light unit 224. The camera unit 222 connects to the endoscope 221 at its proximal end and couples into the optics there, while the light unit 224 couples into the light port of the endoscope 221.

Figure 10:
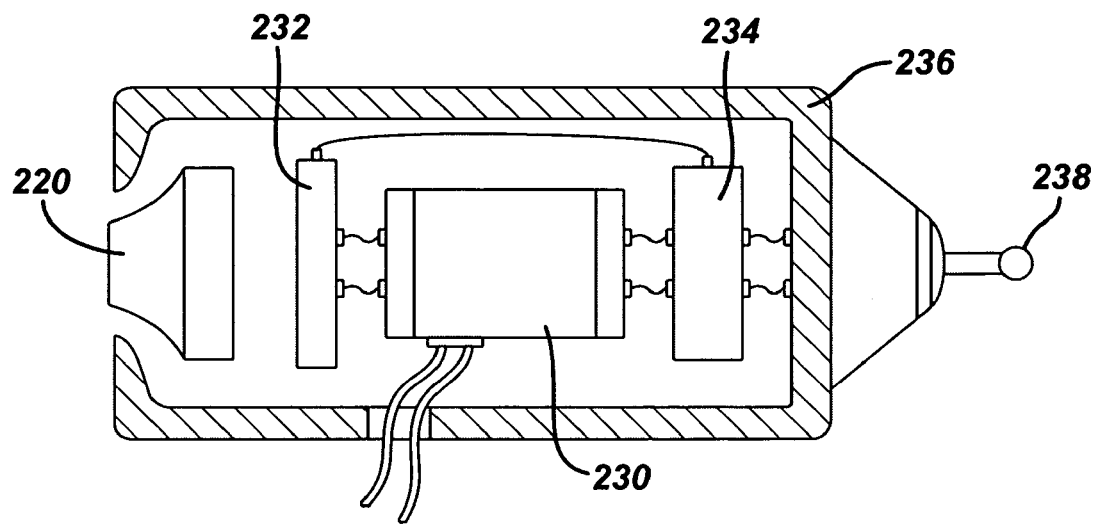
FIG. 10 shows a cross sectional view of the camera unit of FIG. 9.

FIG. 10 shows a cross sectional view of the camera unit 222. The camera unit further comprises a power source 230, an imaging chip 232, a transmission circuit 234, a signal transmission means 238 and a body 236. The imaging chip 232 is placed so that the image carried through the optics of the endoscope 221 is focused onto the imaging chip 232. The imaging chip 232 comprises three major components; the image array, the timing and control circuits and the video processing circuits. The image array is composed of individual pixels that convert the intensity of light shown on it into electrical signals and in some models converts this electrical signal into a digital signal. The video processing circuit reads these signals and formats it into a signal that is readable by the display, such as an NTSC or PAL signal. It is known to those skilled in the art that each of these three functions can be separated into different locations and chips. The image array can be constructed from either a CMOS or a CCD technology. If the image array is based on the CMOS technology then all three processes can be included into a single chip design. An example of a single chip design would be the Omnivision OV7910. This chip has two wires for power input and two for an NTSC signal output. The power supply 230 is connected to the imaging chip 232, the transmission circuit 234 and the power cord. The imaging chip 232 is connected to the transmission circuit 234 so that the signal created by the imaging chip 232 is passed to it. The transmission circuit 234 is operatively connected to the signal transmission means 238 so that the signal is transmitted to a remote display system 22. Although the signal transmission means in FIG. 10 is shown as a wireless connection, it is obvious that this connection could also be a hard-wired one.

Figure 11:
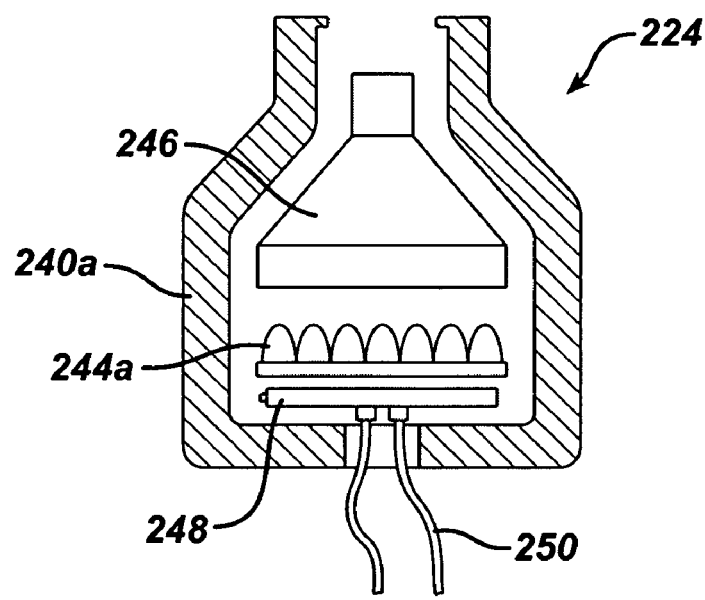
FIGS. 11 and 12 show cross sectional views of alternate embodiments of the light unit shown in FIG. 9.
Figure 12:
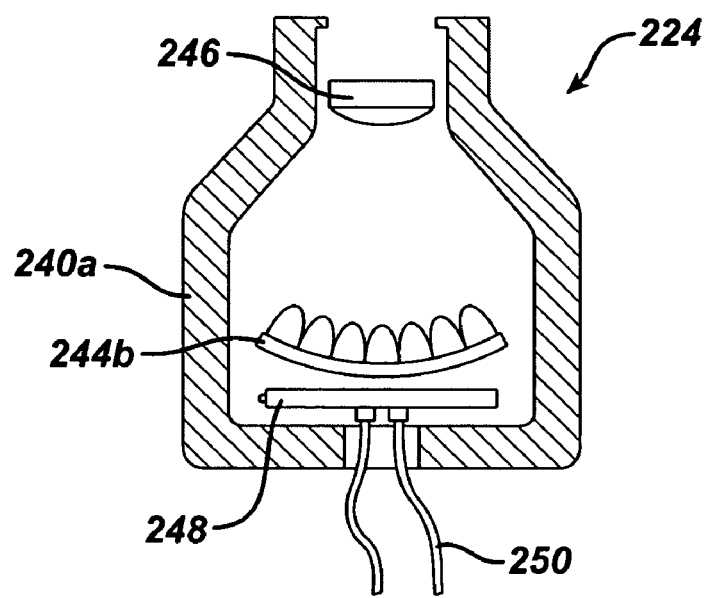

FIGS. 11 and 12 show cross sectional views of alternate embodiments of the light unit 224. Each embodiment comprises a light unit body 240a, b, a white light source 244a, b, a collimator 246a, b, and a circuit board 248a, b. The top of the light unit body is designed in such a way as to be operatively connected to the light port of the endoscope 221. Inside the light unit body, the white light source 244a, b is connected to the circuit board 248a, b. The circuit boards are connected to the power cord 250 and delivers power from the power supply to the white light source 244a, b. In FIG. 11 the white light source 244a is arranged in a planar fashion and the collimator 246a is designed to concentrate and collimate the light generated by the white light source into the light port of the endoscope 221. In FIG. 12 the white light source 244b is arranged in an arc so that its light is focused on a collimator lens system 246b. In this embodiment the collimator is a lens that will concentrate and collimate the light into the light port of the endoscope 221.

The foregoing description of several expressions of embodiments and methods of the invention has been presented for purposes of illustration. It is not intended to be exhaustive or to limit the invention to the precise forms and procedures disclosed, and obviously many modifications and variations are possible in light of the above teaching. For example, as would be apparent to those skilled in the art, the disclosures herein of the ultrasonic systems and methods have equal application in robotic assisted surgery taking into account the obvious modifications of the invention to be compatible with such a robotic system. It is intended that the scope of the invention be defined by the claims appended hereto.

We claim:

1. An endoscope comprising:
   a) a tube with a proximal end and a distal end and defining a longitudinal axis, the distal end comprising a light guide defining a lumen, the light guide comprising:
      i) a collimator segment; and
      a transmission segment distal to the collimator segment and having a smaller cross section than the collimator segment;
   b) a video camera positioned within the lumen of the light guide; and
   c) a white light source positioned at the distal end proximal to the video camera and optically coupled to the collimator segment of the light guide.

2. The endoscope of claim 1 wherein, the white light source comprises at least one LED.

3. The endoscope of claim 2, wherein the at least one LED comprises a plurality of photodiodes contained within a single package.

4. The endoscope of claim 3, wherein the plurality of photodiodes comprises a collection of red, blue and green LEDs in a ratio such that the resultant emitted light is perceived to be white.

5. The endoscope of claim 2, wherein the white light source comprises a collection of red, blue and green LEDs in a ratio such that the resultant emitted light is perceived to be white.

6. The endoscope of claim 1, wherein the white light source comprises at least one tungsten bulb.

7. The endoscope of claim 1, wherein the collimator segment defines a reflecting angle with respect to the longitudinal axis of less than 60 degrees.

8. The endoscope of claim 1, wherein the light guide is comprised of a single molded piece.

9. The endoscope of claim 1, wherein the light guide comprises at least one connected segment.

10. The endoscope of claim 9, wherein one connected segment is a phosphorescent material.

11. The endoscope of claim 9, wherein a plurality of connected segments are composed of a graded index optical material.

12. The endoscope of claim 11, wherein the connected segments are comprised of optical fibers.

13. The endoscope of claim 1 further comprising a battery power supply connected to the video camera and the white light source.

* * * * *